United States Patent [19]

Linder et al.

[11] 4,132,615
[45] Jan. 2, 1979

[54] INTERNAL COMBUSTION ENGINE EXHAUST GAS OXYGEN SENSOR AND CATALYZER COMBINATION

[75] Inventors: Ernst Linder, Mühlacker; Leo Steinke, Hegnach; Franz Rieger, Wasseralfingen, all of Germany

[73] Assignee: Robert Bosch GmbH, Stuttgart, Germany

[21] Appl. No.: 747,480

[22] Filed: Dec. 6, 1976

Related U.S. Application Data

[63] Continuation of Ser. No. 555,870, Mar. 6, 1975, abandoned.

[30]     Foreign Application Priority Data

Apr. 5, 1975 [DE]   Fed. Rep. of Germany ....... 2416629

[51] Int. Cl.$^2$ ........................................... G01N 27/46
[52] U.S. Cl. .......................... 204/195 S; 123/119 E; 423/213.5; 204/1 S
[58] Field of Search ................ 204/15, 195 S; 60/276; 123/119 E; 423/213.5

[56]              References Cited
            U.S. PATENT DOCUMENTS

| | | | |
|---|---|---|---|
| 3,189,563 | 6/1965 | Hauel | 23/288 R |
| 3,544,264 | 12/1970 | Hardison | 423/213.7 |
| 3,616,274 | 10/1971 | Eddy | 60/276 |
| 3,654,111 | 4/1972 | Csuros | 204/195 S |
| 3,768,259 | 10/1973 | Carnahan et al. | 204/195 S |
| 3,835,012 | 9/1974 | Hemak | 204/195 S |
| 3,841,987 | 10/1974 | Friese et al. | 204/195 S |
| 3,844,920 | 10/1974 | Burgett et al. | 204/195 S |
| 3,935,089 | 1/1976 | Togawa et al. | 204/195 S |
| 3,981,785 | 9/1976 | Sandler | 204/195 S |

FOREIGN PATENT DOCUMENTS 1511066  12/1967   France ................................ 204/195 S Primary Examiner—T. Tung
Attorney, Agent, or Firm—Flynn & Frishauf

[57]          ABSTRACT

To avoid temperature shock and mechanical damage to oxygen sensors with ion conductive solid electrolytes exposed to the exhaust gases of internal combustion engines, a catalyst, for example in the form of aluminum oxide pellets having a catalyzing surface layer, is located to surround the oxygen sensor, or just in advance of the oxygen sensor in a bypass pipe, branching off from the exhaust gas pipe of the engine to take samples of the exhaust gases so that the sensor and catalyst form an assembly, or sensing combination. The catalyzing layer may be platinum, or a platinum metal, or an alloy of platinum with aluminum, cobalt, nickel, or chromium, or may be mineral wool, or wool of glass, or asbestos fibers having their surface coated with any of the foregoing catalysts.

21 Claims, 2 Drawing Figures

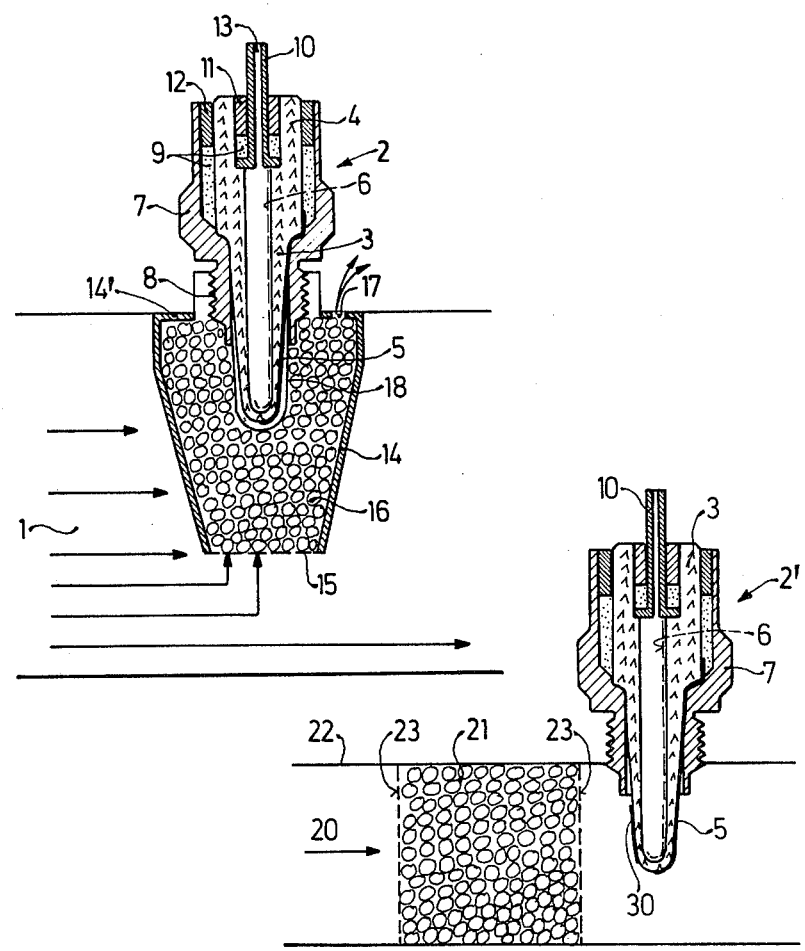

INTERNAL COMBUSTION ENGINE EXHAUST GAS OXYGEN SENSOR AND CATALYZER COMBINATION

This is a continuation of application Ser. No. 555,870, filed Mar. 6, 1975, now abandoned.

Cross reference to related patent: U.S. Pat. No. 3,841,987.

The present invention relates to the field of determining the oxygen content in exhaust gases from an internal combustion engine, and more particularly to a sensing element and gas catalyzing combination having an ion conductive solid electrolyte to determine the oxygen content in the gases to which the sensor is exposed.

BACKGROUND AND PRIOR ART

Internal combustion engines, and particularly automotive-type internal combustion engines, have exhaust gases which include carbon monoxide (CO), unburned, or partially burned hydrocarbons (CH) and nitrogen oxides ($NO_x$), all of which contribute to air pollution. These substances in the exhaust gases from the engine should be reduced to a minimum value in order to reduce, or eliminate, air pollution. The CO and CH components of the exhaust gases should be brought, to the extent possible, into the highest oxidation stage, that is, $CO_2$ and, in the case of the hydrocarbon compounds, $CO_2$ and water. The $NO_x$ compounds should be treated to provide elementary nitrogen and oxygen. Treating the noxious components of the internal combustion engines so that the harmless exhaust compounds, carbon dioxide, nitrogen and water result, can be done by various means. For example, the exhaust gases can be subjected to subsequent combustion, that is, to after-burning, by conducting the exhaust gases over a catalyst at temperatures above about 600° C. The composition of the exhaust gases must, however, be so set that practically complete reaction of the exhaust gases is possible to form the harmless exhaust compounds. In other words, the relationship of air to fuel supplied to the engine, and hence exhausted from the engine, must be approximately at the stoichiometric value. The concept of an air number $\lambda$ has been introduced, and stoichiometric conditions prevail when $\lambda = 1$. When $\lambda$ is less than 1, or almost equal to 1, no oxygen is present which is in excess of the balance value for the various possible reactions; when $\lambda$ is greater than 1, excess oxygen is present in the exhaust gases. When $\lambda = 1$, the exhaust gas changes between reducing and oxidizing state.

To maintain the exhaust gases at a value of $\lambda = 1$, the oxygen content in the exhaust gases must be determined and a control system then commanded thereby to control the respective amount of fuel and air being supplied to the engine so that the exhaust gases will have the desired composition.

Electrochemical sensors have been proposed which cooperate with electrical measuring and control circuits. Such sensors utilize the principle of ion conductive solid electrolytes, determining oxygen concentration. The sensors are so designed that, upon transition of the air number from a value less than unity to a value greater than unity, that is, at $\lambda = 1$, a sharp voltage jump is sensed. Thus, at the desired value $\lambda =$ unity, a sharp, easily recognized and evaluated control signal is provided by the sensor. This is a substantial advantage of these elements and permits reliable evaluation of the oxygen content in the exhaust gases.

Sharp electrical voltage jumps derived from a sensor can be obtained only if the components of the exhaust gases are in essentially thermo-dynamic balance. Unfortunately, this is hardly ever the case in actual operation.

Sensors and sensing circuits and control circuits have been described which utilize a sensor constructed to have an electron conductive porous layer at the surface exposed to the exhaust gases. This porous layer catalyzes the gas equilibrium. This catalyzing porous layer is covered at the outside with a porous catalytically inactive layer, acting as a protective coating. This porous protective coating — over the catalyzing layer — contributes to homogenization of the exhaust gases in advance of contact of the exhaust gases with the catalyzing layer. The reaction speed of the sensor, and thus the response time of the entire control circuit is thereby reduced. Additionally, the speed of gas passing by, or reaching, the surface of the catalyst is decreased so that, within the protective coating, the dwell time of the gases at the surface of the catalyst is increased.

The electro-chemical sensor, constructed in layers, previously had been exposed directly to the exhaust gases. The sensor, therefore, is exposed to rugged conditions, particularly affecting its mechanical strength. The sensor is exposed to such mechanical influences as temperature shocks, and impingement by particles, so that the ceramic material of which the sensor is constructed, as well as the layers and coatings applied thereto must be capable of withstanding wide swings in temperature, and must be mechanically strong, further, the layers must have excellent mutual adhesion. These high requirements being placed on the sensor make its construction quite costly.

THE INVENTION

It is an object of the present invention to provide an oxygen sensing structure for use in an exhaust gas control system in which oxygen content in the exhaust gases of internal combustion engines can be determined, and in which the temperature sensor is protected against shocks, impingement by particles, and the like, without interfering with the electro-chemical properties of the sensor itself and, desirably, to permit the sensor to be used with known and standardized measuring systems while permitting simple and inexpensive manufacture thereof.

Briefly, to protect the sensor against temperature shocks and bombardment by particles, a catalyst is placed in advance of the sensor — with respect to flow direction of the exhaust gases. The catalyst may consist of pellets or the like, preferably porous, the surface of which is coated with a catalyst layer. Typical carrier pellets may be made of aluminum oxide; the catalyst layer may be, for example, platinum, an alloy of platinum with aluminum, cobalt, nickel, chromium, or other platinum metals, as an alloying component.

The catalyst may also be made by using mineral wool, or fibrous substances, the surfaces of which are coated with a catalyzing layer. A wool of glass or asbestos fibers is particularly suitable, the surfaces of which are coated with the same catalyzing material as that referred to in connection with aluminum oxide pellets.

The invention will be described by way of example with reference to the accompanying drawings, wherein:

FIG. 1 is a schematic longitudinal sectional view through a sensor, and sensing system, in accordance with the present invention, secured in the exhaust pipe of an automotive engine; and FIG. 2 illustrates a sensor located in a bypass sampling tube connected to the exhaust pipe of an automotive, internal combustion engine.

The main exhaust pipe 1 of an automotive engine (not shown) is formed with an opening in which the sensor is mounted. The sensor, thus, is exposed directly to the stream of exhaust gases from the engine. The sensing element 2 as the main component of the sensor or sensing system consists of a solid electrolyte tube 3, closed at one end, and having an open end formed with a stub tube 4. The solid electrolyte tube 3 is made of stabilized cubic zirconium dioxide. The outer surface of the solid electrolyte 3 has an outer electrode 5 applied thereto. The hollow space within the tube 3 has an inner electrode 6 applied thereto. Electrodes 5 and 6 are formed as conductive strips made of platinum, applied by painting a line of a platinum suspension on the electrolyte body 3 and then firing the tube 3. The conductive strips forming the electrodes 5, 6 extend to the end 4 of the tube. The solid electrolyte 3, together with the end portion 4, is seated in a steel socket 7 which has a thread 8 to secure the sensor in position within a retainer 14 for catalyzing material 16. An electrically conductive press connection 9 is located between the end portion 4 of the tube 3 and the socket 7. This press, which may be melted in, is used to mechanically connect the solid electrolyte tube into the socket 7 and simultaneously provides electrical contact between the outer electrode 5 and the socket 7. It also provides for sealing of the solid electrolyte tube and the socket.

A contact flag 10 is located in the outer end of the hollow space within the solid electrolyte tube. The contact flag 10 is mechanically secured in the end portion 4 of the tube 3 and is in electrical contact with the inner electrode 6. The press 9, melted in, provides for mechanical holding of the contact flag 10 and, likewise, for electrical connection thereof with the inner electrode 6. Steel rings 11, 12, which are press-fitted, mechanically protect the ends of the melted in press 9, and are used to compress the electrically conductive connection 9, so that the melt 9 will provide good electrical contact between the respective electrode 5, 6 and the steel jacket 7 on the one hand, and the contact flag 10, on the other. Contact flag 10 is formed with a bore 13 which provides free entrance of ambient air into the hollow interior of the tube 3. This ambient air provides the reference oxygen level for the sensor.

The portion of the sensor 2 which extends into the main stream of the exhaust gases is surrounded by catalyzing material 16, in the retainer 14 formed as a conical pipe stub made of high-quality steel, for example special, super-refined steel, stainless steel, or the like. The conical tube or stub 14 is closed off at the bottom by a wire mesh 15, likewise made of high-quality steel, which may be similar to that of the conical tube 14. A catalyst 16, which consists of loose, poured material, is located in the conical tube 14 surrounding sensor 2. The loose, catalyst mass 16 preferably consists of aluminum oxide pellets of, for example, about 3 mm diameter, the surface of which is coated with a thin layer of platinum. The upper portion of the tube 14 which fits against the inner circumference of the pipe 1, is formed with a break, groove, or other opening 17. As shown, the conical tube 14 is formed with an in-turned flange 14', in which the opening 17 is located. This opening 17 is in communication either with ambient outside air or the opening may be located downstream (with respect to flow of exhaust gases) so that a connection to either ambient air or the downstream side of the exhaust gas pipe 1 is provided in order to prevent dead gas accumulation within the tube 14 and to induce flow of gas therethrough. Thus, a portion of the exhaust gases and forming a sampling gas portion is conducted through the loose catalyst mass and to the surface of the solid electrolyte tube 3. Dead gas volumes within the sensor system are thereby avoided, which might otherwise cause reduction in response time of the entire measuring system, due to excessive deceleration of gas flow past the sensor tube 3.

The loose catalyst 16 should, preferably, not touch the outer surface of the solid electrolyte tube. To prevent such contact, the outer surface of the solid electrolyte tube is surrounded by a wire mesh 18, likewise of high-quality, special steel, secured in the lower portion of the socket element 7. The wire mesh 18, for example in the form of a depending nipple, or cup-shaped may, in turn, be coated with a platinum layer in order to increase the catalytic effect, that is, to further improve the catalytically obtained gas equilibrium, should the catalyst 16 not be fully effective anymore. The stub 14, closed off by mesh 15, and separated from the sensor unit by mesh 18 forms a holding basket for the loose catalyst 16, from which the sensing unit can be removed by unscrewing it by threads 8.

The sensor 2' illustrated in FIG. 2 is similar to that described in connection with FIG. 1, except that the protective mesh or screen 18 is not absolutely necessary, although it may be used. Contrary to the embodiment of FIG. 1, however, the sensor is not located in the main gas stream of the exhaust pipe, but rather is located in a bypass 20, branching off from the main exhaust gas stream schematically indicated at 20', to provide a sampling stream in a bypass or sampling branch pipe 22. Catalyst material 21 is located in the sampling pipe 22 and completely fills the cross section thereof, as seen in FIG. 2. Mesh or sieve-like cross plates 23 retain the catalyst 21 in position. These mesh or sieve-like cross elements 23 preferably are made of special high-quality steel, similar to the material of mesh 15 (FIG. 1). The solid electrolyte tube has an outer electrode 5, in the form of a conductive strip thereon. To further improve the catalytic effect by catalysts 16, 21, respectively, the outer surface of the electrolyte tube may be coated with an electron conductive layer 30 which catalyzes the equilibrium condition of the gas balance. Such a catalyzing layer must be porous so that the exhaust gas can reach the electrolyte surface of the tube 3. This layer may consist of platinum, or an alloy of platinum with aluminum, cobalt, nickel, chromium, or other platinum metals as alloying components; or may be an oxide system such as copper-chrome oxide doped, if desired, with barium oxide or nickel oxide; or it may be lanthanium-cobalt oxide, doped, if desired, with strontium oxide. The sensor can be removed from the bypass pipe 22 as a unit independently of the catalytic material 21.

Various changes and modifications may be made within the scope of the inventive concept.

We claim:

1. Internal combustion engine exhaust gas sensor and gas catalyzer combination unit to provide an electrical output signal indicative of the presence of oxygen in the exhaust gases being conducted through a duct means (1) from an internal combustion engine comprising an oxygen sensing element including an ion conductive solid electrolyte body (3) shaped to form a tube, open at one end, the closed end of the tube being adapted to be exposed to the exhaust gases from the internal combustion engine, a first electrode (5) applied to the outside surface of the tube, and a second electrode (6) applied to the inside of the tube, the sensing signal indicative of presence or absence of oxygen in the exhaust gas being measured across said electrodes (5,6);

and a protective and catalyst unit to catalyze the gas equilibrium of gas to which the sensing unit is exposed and to protect the outside of both the body (3) and the first electrode (5) thereon, including a spacing tube (18) of mesh material surrounding the ion conductive solid electrolyte body (3), with clearance;

a surrounding outer essentially tubular holding element (14, 15) extending into the exhaust gas stream and located to surround the spacing tube (18) and the ion conductive solid electrolyte tube (3) and leaving a space between the spacing tube and the outer holding element to form a chamber;

a catalyst means (16) comprising a carrier coated at least in part with a layer of catalytic material located in said chamber;

and means providing for flow of a sampling gas portion through said chamber comprising at least two openings (15, 17) formed in said outer holding element (14) and located to induce flow of exhaust gases therethrough, whereby the catalyst will be spaced from the surface of said electrolyte body and will be upstream thereof, with respect to the flow direction of the sampling portion of the stream of exhaust gases through the duct means (1) to which the sensor and gas catalyzer combination is adapted to be exposed.

2. Unit according to claim 1, wherein the holding element includes an essentially tubular portion and a bottom closing portion, said bottom closing portion comprising a mesh screen (15) closing off the tubular portion at the region where the holding element is exposed to the stream of gas flow in said duct means, said tubular portion, the mesh screen, and the mesh spacing tube (18) defining said chamber therebetween and forming a holding basket for said catalyst means.

3. Unit according to claim 1, wherein one of said openings (17) is in communication with ambient air.

4. Unit according to claim 1, including means on said sensor to locate the sensor and the outer tube in the main exhaust gas stream from the internal combustion engine.

5. Unit according to claim 1 wherein at least a portion of the outer surface of the ion conductive solid electrolyte tube (3) has an electron conductive layer (30) applied thereto, said layer being porous and catalyzing the gas equilibrium condition at the surface of the ion conductive tube (3).

6. Unit according to claim 1, wherein the carrier of the catalyst means (16,) comprises pellet-like elements having their surfaces coated with the layer of catalytic material.

7. Unit according to claim 6, wherein said pellets are porous.

8. Unit according to claim 6, wherein said pellets comprise aluminum oxide.

9. Unit according to claim 1 wherein the layer of catalytic material comprises at least one of: platinum, an alloy of platinum with at least one of: aluminum, cobalt, nickel, chromium, or another platinum metal.

10. Unit according to claim 1 wherein the carrier of the catalyst means comprises mineral wool having at least a portion of its surface coated with the layer of catalytic material.

11. Unit according to claim 10, wherein the carrier of the catalyst means comprises at least one of: glass wool, formed of glass fibers; and asbestos wool, formed of asbestos fibers.

12. Unit according to claim 1, wherein the carrier is of catalytically inactive material.

13. Internal combustion engine exhaust gas sensor and gas catalyzer combination unit for installation in the exhaust system of an internal combustion engine, to provide an electrical output signal indicative of the presence of oxygen in the exhaust gases from the engine having an oxygen sensing subunit comprising an ion conductive solid electrolyte tube (3) which is closed at one end and open at the other, the open end being adapted to be in gas communication with ambient atmosphere to provide a reference oxygen level, the surface of the tube surrounding the closed end being adapted for exposure to the exhaust gases from the engine;

electrode means (5, 6) located at the inner and outer surfaces, respectively, of the tube; and a catalyst subunit, to catalyze the gas equilibrium located with respect to contact of the gas with the tube in advance thereof, so as to be interposed between the gas and the outside surface of the tube comprising a catalyst including a carrier material and a layer of catalytically active material at least in part coating the carrier material;

and retaining and positioning means (18, 14, 15) retaining said catalyst carrier material coated with the catalytically active material and positioning said coated carrier material adjacent to, and spaced from the electrolyte tube (3) to prevent physical contact with the outer surface of the tube while shielding the tube from direct contact with non-catalyzed gas from the engine, including a mesh tube spaced from and surrounding the solid electrolyte tube (14);

and a perforate, basket-like holder (14, 15) surrounding said mesh tube to form a chamber therewith and positioning and confining the carrier material coated with the catalytically active material in said chamber;

and wherein said sensing subunit forms a separate assembly, removable from the catalyst subunit and separable as an individual subunit from the sensor-catalyzer combination unit.

14. Unit according to claim 13, wherein at least a portion of the outer surface of the ion conductive solid electrolyte tube (3) has an electron conductive layer (30) applied thereto, said layer being porous and catalyzing the gas equilibrium condition at the surface of the ion conductive tube (3).

15. Unit according to claim 13, wherein the carrier of the catalyst means (16,) comprises pellet-like elements having their surfaces coated with the layer of catalytic material.

16. Unit according to claim 15, wherein said pellets are porous.

17. Unit according to claim 15, wherein said pellets comprise aluminum oxide.

18. Unit according to claim 13, wherein the layer of catalytic material comprises at least one of: platinum; an alloy of platinum with at least one of: aluminum, cobalt, nickel, chromium, or another platinum metal.

19. Unit according to claim 13, wherein the carrier of the catalyst means comprises mineral wool having at least a portion of its surface coated with the layer of catalytic material.

20. Unit according to claim 19, wherein the carrier of the catalyst means comprises at least one of: glass wool, formed of glass fibers; and asbestos wool, formed of asbestos fibers.

21. Sensor according to claim 13, wherein the carrier is of catalytically inactive material.

* * * * *

UNITED STATES PATENT AND TRADEMARK OFFICE
CERTIFICATE OF CORRECTION

PATENT NO. : 4,132,615
DATED : Jan. 2, 1979
INVENTOR(S) : Ernst LINDER et al

It is certified that error appears in the above-identified patent and that said Letters Patent are hereby corrected as shown below:

Page 1, line [30] Apr. 5, 1975 should be -- April 5, 1974

Signed and Sealed this

Eighth Day of May 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,132,615
DATED : January 2, 1979
INVENTOR(S) : Ernst Linder et al.

It is certified that error appears in the above-identified patent and that said Letters Patent are hereby corrected as shown below:

Column 2, line 40, after "the" delete "temperature"
line 41, insert --temperature-- before "shocks".

Signed and Sealed this

Third Day of July 1979

[SEAL]

Attest:

Attesting Officer

LUTRELLE F. PARKER
Acting Commissioner of Patents and Trademarks